(12) United States Patent
Edginton et al.

(10) Patent No.: US 8,337,472 B2
(45) Date of Patent: Dec. 25, 2012

(54) SHEATH REMOVER DEVICE

(75) Inventors: Alex Edginton, Oxon (GB);
Christopher William Hudson, Oxon (GB)

(73) Assignee: Owen Mumford Limited, Oxfordshire (GB)

(*) Notice: Subject to any disclaimer, the term of this patent is extended or adjusted under 35 U.S.C. 154(b) by 101 days.

(21) Appl. No.: 12/811,642

(22) PCT Filed: Dec. 31, 2008

(86) PCT No.: PCT/GB2008/004293
§ 371 (c)(1),
(2), (4) Date: Jul. 2, 2010

(87) PCT Pub. No.: WO2009/087355
PCT Pub. Date: Jul. 16, 2009

(65) Prior Publication Data
US 2010/0286620 A1 Nov. 11, 2010

(30) Foreign Application Priority Data
Jan. 4, 2008 (GB) .................................. 0800103.4

(51) Int. Cl.
*A61M 5/32* (2006.01)
*A61M 5/00* (2006.01)
*B65D 83/10* (2006.01)
(52) U.S. Cl. .................... 604/263; 604/192; 206/370
(58) Field of Classification Search .................. 604/110, 604/192, 193, 197, 198, 263; 206/363–370
See application file for complete search history.

(56) References Cited

U.S. PATENT DOCUMENTS

| | | | | |
|---|---|---|---|---|
| 4,986,817 | A * | 1/1991 | Code | 604/192 |
| 5,718,689 | A * | 2/1998 | Stevenson | 604/192 |
| 8,048,029 | B2 * | 11/2011 | Gillespie et al. | 604/110 |
| 2006/0229652 | A1 * | 10/2006 | Iio et al. | 606/182 |
| 2007/0173772 | A1 | 7/2007 | Liversidge | |

FOREIGN PATENT DOCUMENTS

| | | |
|---|---|---|
| WO | 03/051423 | 6/2003 |
| WO | 2007/036676 | 4/2007 |
| WO | 2007/132353 | 11/2007 |

OTHER PUBLICATIONS

International Search Report dated Apr. 24, 2009, from corresponding PCT application.

* cited by examiner

*Primary Examiner* — Nicholas Lucchesi
*Assistant Examiner* — Nathan R Price
(74) *Attorney, Agent, or Firm* — Young & Thompson

(57) ABSTRACT

A sheath remover device is of elongate tubular form having a sheath capture region at one end and a passage along which a captured sheath may pass from the capture region. A plurality of latching fingers, each with an internally directed latch, are equi-spaced in the capture region. Two further inwardly directed latches are on the cut out regions. The sheath remover is designed so that, a sheath already disposed in the sheath capture region is pushed along the passage away from the sheath capture region when the remover is offered up to and engages the subsequent sheath. The spacing of the latches and is such that the earlier sheath is not released from latches until the latches have securely engaged in the subsequent sheath, thereby providing an indication of secure engagement of the subsequent sheath. The sheath remover may also be used as a cap and/or a cocking rod.

22 Claims, 5 Drawing Sheets

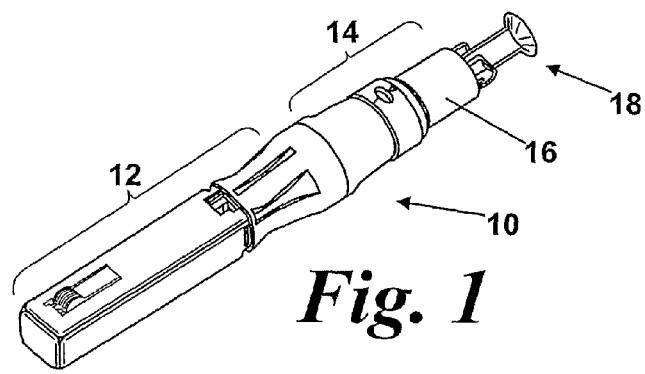
Fig. 1
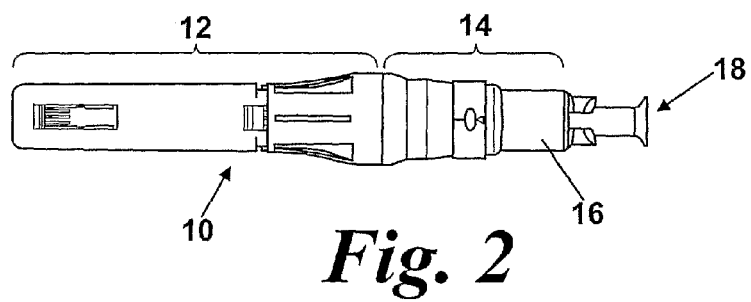
Fig. 2
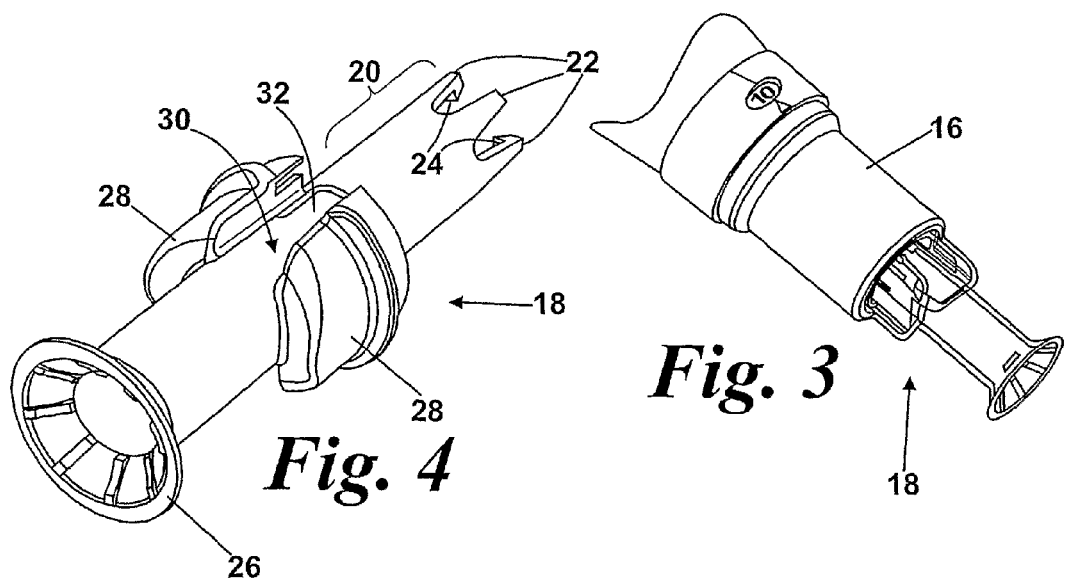
Fig. 4
Fig. 3

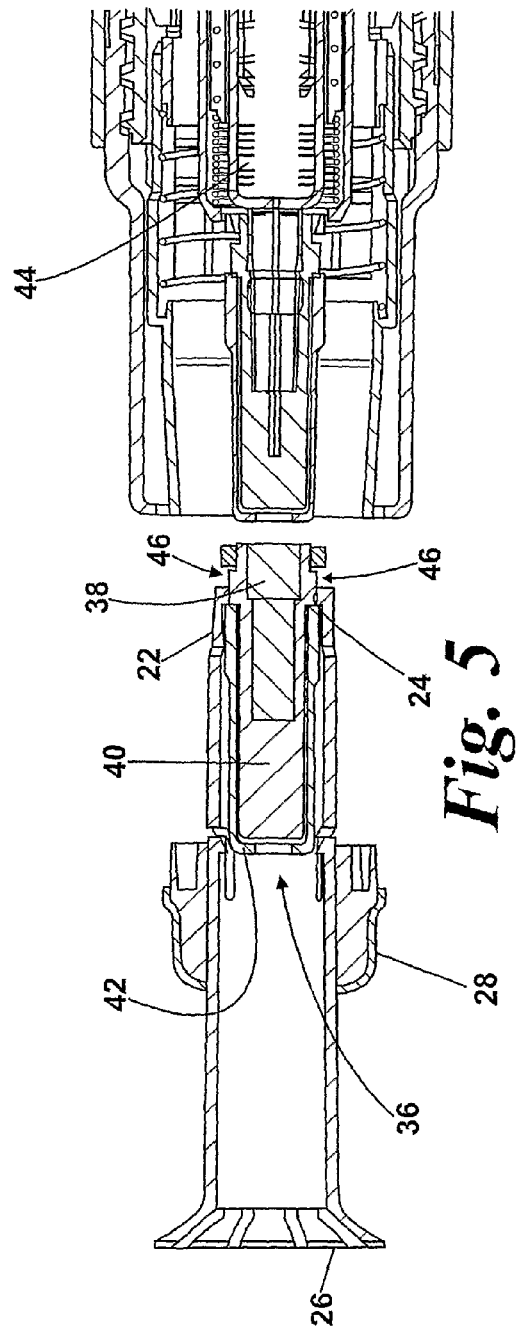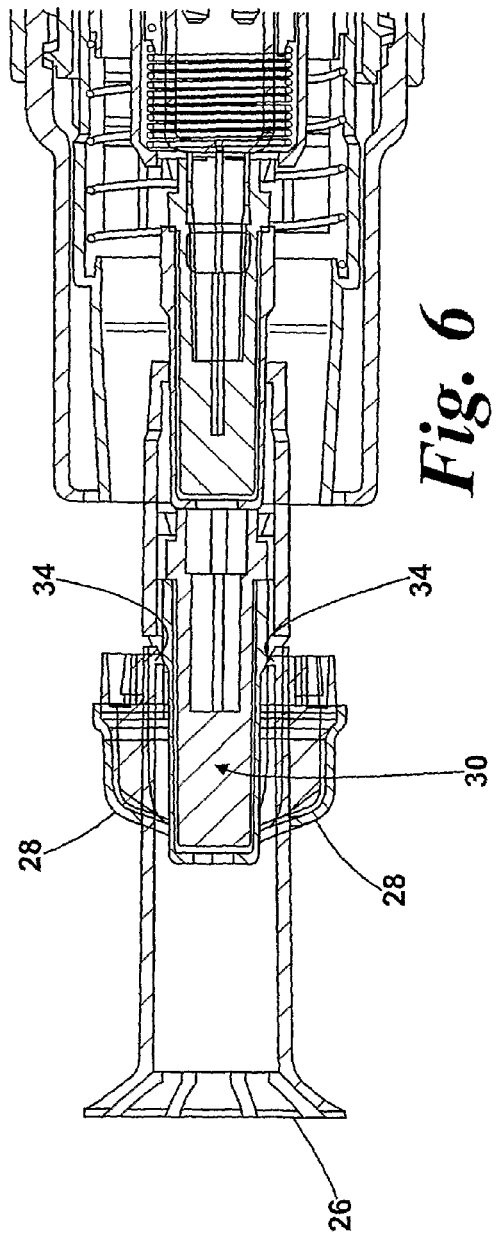

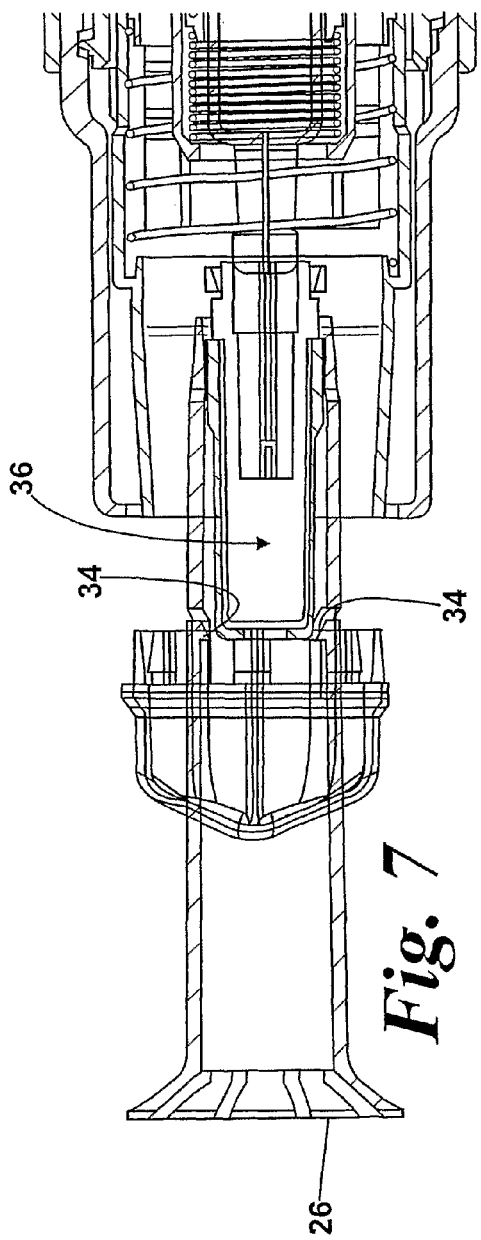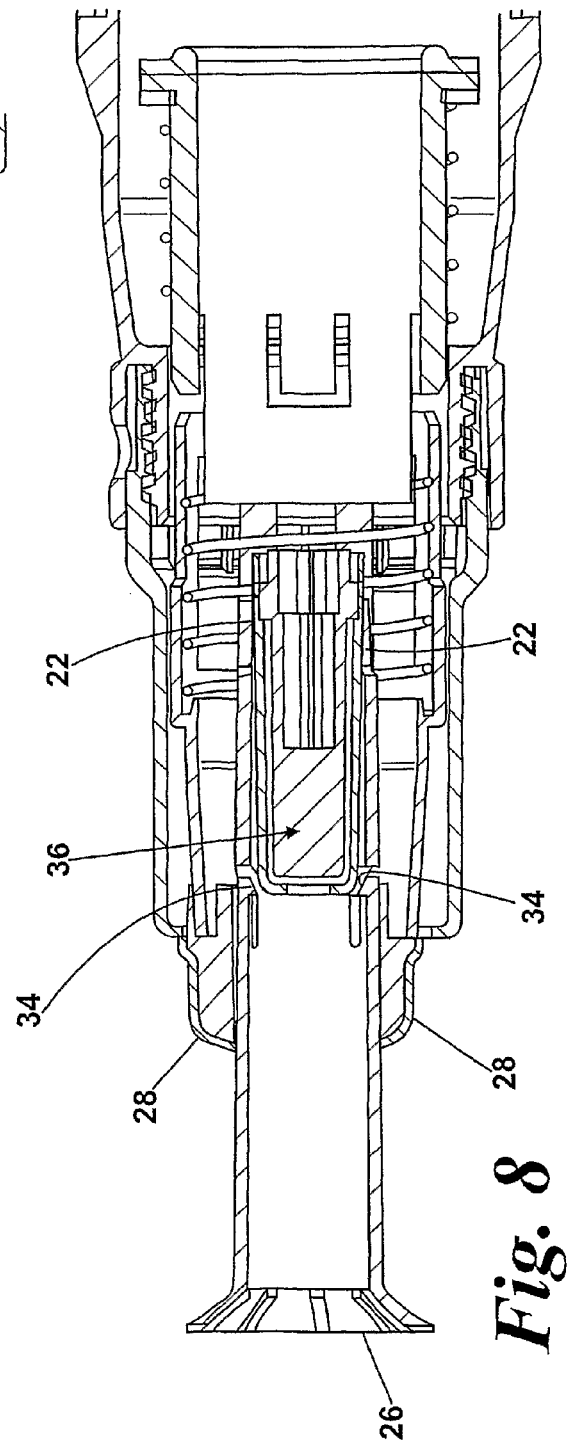
Fig. 7
Fig. 8

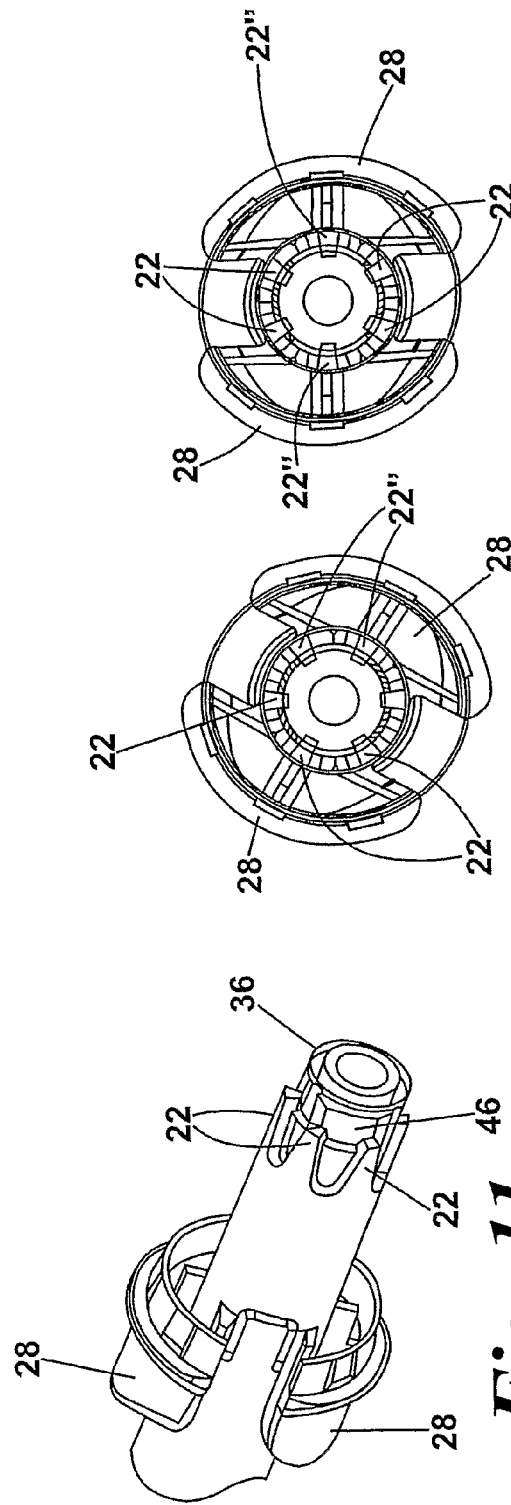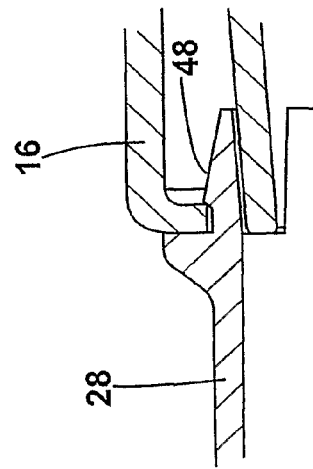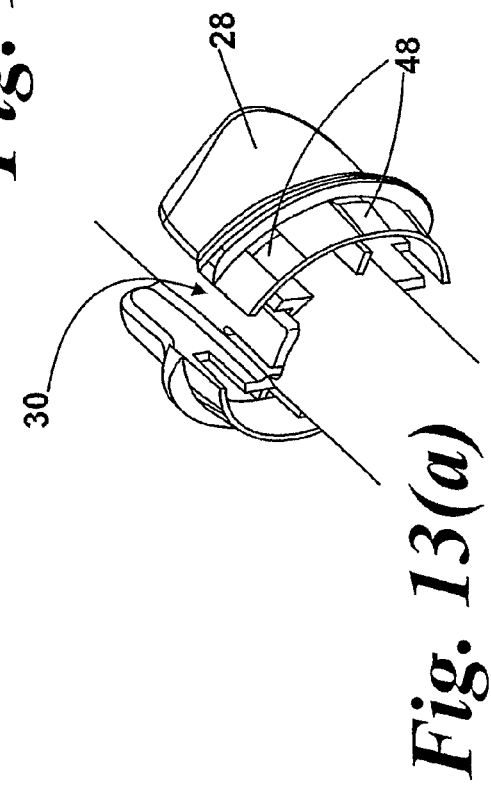

SHEATH REMOVER DEVICE

This invention relates to a sheath remover device for removing a sheath from a syringe needle located within a housing of an injection device, and to such injection devices.

In many reusable injection devices the drug is supplied pre-filled into a syringe with a needle attached, the needle being covered by a needle sheath, sometimes referred to as a boot. The needle sheath both keeps the needles sterile and also protects against needle-stick injuries. The needle sheath is often quite tightly attached to the needle for safety purposes and it is desirable not to remove the needle sheath until after the pre-filled syringe has been safely located within an injector housing which otherwise shrouds the needle. Given the strength of the attachment of the sheath to the needle, it is important to have a reliable way of removing the needle sheath. As indicated, the syringe and needle sheath are typically contained within a housing which means that the sheath is (intentionally) inaccessible by hand. The sheath is therefore typically removed by some form of sheath remover. It is possible to supply a pre-filled syringe with both the needle sheath attached and a needle remover attached to the sheath, but this means that a needle sheath remover must be supplied with each syringe which is wasteful.

Accordingly, we have designed a needle sheath remover which is capable of being reused many times yet which allows easy disposal of the removed sheaths.

In one aspect of this invention, there is provided a sheath remover for use in removing a sheath from a needle prior to an injection, said sheath remover comprising:
  an elongate sheath passageway having a sheath capture region at one end and along which a sheath may pass away from the sheath capture region;
  a sheath gripping arrangement disposed in said sheath capture region and adapted in use to be engagable with a needle sheath when offered up thereto and to grip the sheath sufficiently to enable the sheath remover to remove the sheath from the needle as the sheath remover is pulled away from the syringe,
  wherein said sheath remover is adapted such that, in use, a sheath already disposed in the sheath capture region is pushed along the passage, away from the sheath capture region, when the sheath remover is offered up to, and engages a subsequent sheath.

In this manner, each time the sheath remover is used, offering up the remover to a new sheath dislodges the previous sheath and pushes it down the sheath passageway. Thus, in preferred embodiments the user does not have to manually detach a removed sheath from the remover because this is done by the next sheath.

Preferably, the sheath passageway comprising a solid-walled tube open at least one end. Although it would be possible for the other end to disgorge into a chamber or the like, it is preferred for the tube to be open at both ends.

Although said sheath gripping arrangement could grip by friction alone, high attachment strength between the sheath and the syringe means that it is preferable for the sheath gripping arrangement to comprise one or more latch elements designed to latch over a shoulder or recess on the sheath as the sheath remover is offered up to a sheath in use. This provides a mechanical inter-engagement capable of transfer of high separation forces. The preferred latch element or elements allow movement of a retained sheath from said sheath capture region further into said passageway when pushed in that direction by a subsequent sheath.

The latch element or elements may take a number of different forms but preferably comprise a plurality of latch fingers. Where the sheath is of a general form having diametrically opposed windows provided in a generally cylindrical portion, and each window subtends a given arc, said latch fingers are preferably disposed equi-angularly and at a pitch to ensure that at least two latch fingers latch into each window.

Preferably, the sheath remover includes a further gripping arrangement disposed within said passageway and spaced from said first mentioned gripping arrangement and designed slidably to engage a sheath that is being moved further into the passageway by engagement of the sheath remover with a subsequent sheath.

It is preferred for the further gripping arrangement to be spaced longitudinally from said first mentioned gripping arrangement by a distance which, having regard to the length of the sheath, is such that a subsequent sheath pushes the previous sheath clear of the second gripping arrangement to release it to pass freely along the passageway only when the subsequent sheath has been securely engaged by said first mentioned gripping arrangement. In this way, release of a previous sheath from the further gripping arrangement and its passage along the passageway indicate to the user that the sheath remover is in secure gripping contact with the next sheath. This provides an important advantage because it will be appreciated that often the sheath will be hidden from view and so it is difficult for the user to tell when and whether the next sheath has been securely gripped.

Preferably, at least part of the walls making up the passageway are transparent or apertured such that a sheath displaced by a subsequent sheath is exteriorly visible. Again, sight of the previous sheath passing along the passage gives a clear visual indication to the user of the process of engagement.

Preferably, said sheath remover is removably attachable to said syringe housing in use, for storage. This reduces the likelihood of the sheath remover getting lost and also means that the sheath remover acts as a cover.

The invention also extends to an injection device comprising a housing, a syringe locatable within the housing in use and having a needle covered by a removable sheath, and a sheath remover for removing a sheath from the needle prior to an injection, said sheath remover comprising:
  an elongate sheath passageway having a sheath capture region at one end and along which a sheath may pass away from the sheath capture region;
  a sheath gripping arrangement disposed in said sheath capture region and adapted in use to be engageable with a needle sheath when offered up thereto and to grip the sheath sufficiently to enable to the sheath remover to remove the sheath from the needle as the sheath remover is pulled away from the syringe,
  wherein said sheath remover is adapted such that, in use, a sheath already disposed in the sheath capture region is pushed along the passage, away from the sheath capture region, when the sheath remover is offered up to, and engages a subsequent sheath.

Advantageously, where said injection device has a cockable mechanism, the injection device may be cocked by inserting a portion of said sheath remover into said injection device and using said sheath remover to engage an internal drive mechanism. In this way, the sheath remover serves multiple functions; it functions as a sheath remover to remove the sheath from a needle prior to injection; it serves as a cocking device for cocking the injection device, and it serves a cover for the housing between uses.

In one arrangement, where the injection device includes a depth adjustment collar movably mounted on a forward portion of the housing to adjust the penetration depth of the needle when the device is actuated, the injection device is arranged such that the needle sheath extractor is prevented from engaging a needle sheath unless the depth penetration adjustment is set at or above a preset level. This provides an important safety feature.

Whilst the invention has been described above, it extends to any inventive combination of the features set out above or in the following description.

The invention may be performed in various ways and an embodiment thereof will now be described by way of example only, reference being made to the accompanying drawings, in which:

FIG. 1 is a general perspective view of an injection device fitted with a sheath remover in accordance with this invention;

FIG. 2 is a side view of the injection device of FIG. 1;

FIG. 3 is a detailed enlarged view on the front end of the device showing the sheath remover inserted into the front end of the device adjacent the penetration depth adjuster;

FIG. 4 is a perspective view of the sheath remover when withdrawn from the injection device, but empty;

FIGS. 5 to 8 are cross-sectional views of the sheath remover and the forward end of the injection device through subsequent phases of operation of the sheath remover;

FIG. 11 is a perspective view of the sheath capture region of the sheath remover removed from the injection device and clasping a sheath;

FIGS. 12a and 12b are end views on the sheath capture region of the sheath remover clasping a sheath at different angular orientations, and FIGS. 13a and 13b are detailed views on the latch feature then enables the sheath remover releasably to be latched on the forward end of the injection device.

Figure 9A:
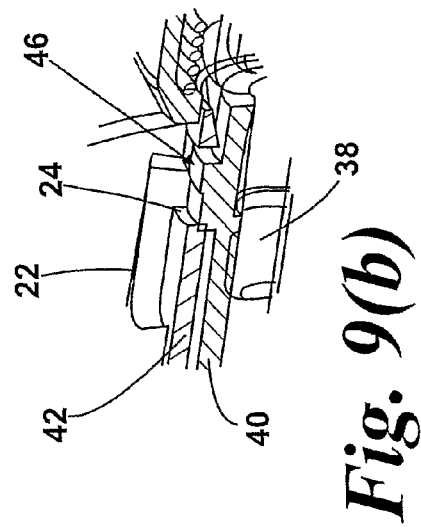
FIGS. 9a and 9b are perspective, cut away views showing engagement of a latching finger of the sheath remover in a window of the sheath.

Referring initially to FIGS. 1 to 4, the injection device 10 illustrated therein has separable rearward and forward housing parts 12 and 14 respectively. A rotationally adjustable penetration depth adjuster 16 is mounted on the forward end of the forward housing portion 14. A sheath remover 18 is shown inserted into the front end of the device here acting as a temporary cap.

Figure 9B:
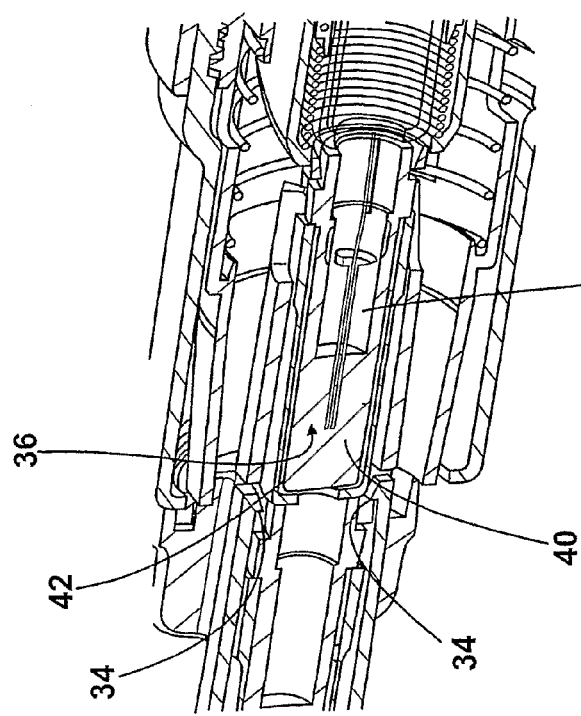
Figure 10:
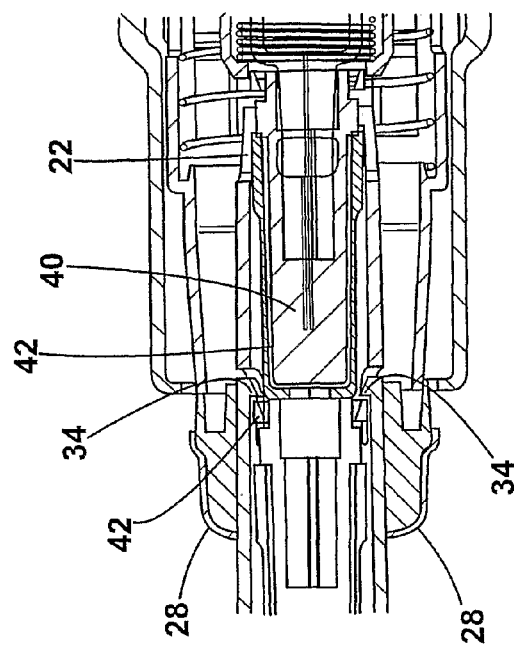
FIG. 10 is a detailed view of the latching features of the sheath remover.

Referring specifically to FIG. 4, the sheath remover 18 has a sheath capture region 20 having, in this example, six latching fingers 22 each with an internally directed latch 24. At the other end, the sheath remover has a trumpet end 26 which facilitates gripping and also provides an abutment surface for cocking the injector. About halfway down the sheath remover there are two diametrically opposed shoulder protrusions 28 which define between them respective diametrically opposed slots 30. The main body of the sheath remover is of open-ended tubular form and, adjacent each of the rear ends of the slots, as viewed in FIG. 4, the cylindrical wall has a U-shaped cut out region 32 which defines, on the inner surface thereof, two further latches 34 (see FIGS. 5 to 9).

For cocking, the trumpet end of the sheath remover locates over the male end of the drive mechanism (not shown). This pushes the plunger of the mechanism back. When cocking the device, the shoulder protrusions 28 are larger in diameter than the open front end of the rearward syringe housing part 12 and so limit the insertion depth. If this distance is less than the distance that the plunger needs to move back to engage its cocking latch (not shown), the device will not cock.

The sheath remover 18 is intended to remove a sheath 36 from a pre-filled syringe inside the injection device. The sheath is illustrated in FIGS. 5 to 9, and is of a typical form which comprises a soft rubber or rubber-like core 38 contained in an intermediate narrow hat shaped member 40 which itself is contained in a hard resilient plastics outer hat element 42. The outer hat member has, at its end adjacent the syringe 44 (hereafter the rearward end) two diametrically opposed windows 46 each of which subtend about 90° and which are provided for handling of the sheath.

In FIG. 5, the sheath remover is shown already with a sheath in it, and aligned for being inserted into the forward end of the injection device 10. The sheath 36 already in the sheath remover may be a previously removed sheath or it may be a 'dummy' sheath that is supplied for first use. It will be noted that the sheath contained in the device is latched with respect to the sheath remover by the latch surfaces 24 on the latch fingers 22 engaging the forward wall of the windows 46 (see FIGS. 9a and b). The forward end of the outer hat 42 is disposed alongside the inwardly directed further latches 34. The internal diameter of the sheath remover body is designed to allow the passage of a sheath through it.

The sheath remover is then pushed into the device so the rear end of the sheath held by the sheath remover engages the forward end of the sheath in the device. Continued pressure pushes the sheath in the sheath remover towards the trumpet end (FIG. 6) and, as this occurs, the inwardly directed latches 34 ride over the outer part of the forward sheath (hereinafter the previous sheath) until eventually the latch fingers 34 snap past the rear end of the previous sheath so the previous sheath is no longer held thereby and may slide down the sheath to the trumpet end. However, the longitudinal positioning of the latching fingers 22 and the further latch 34 is designed so that the previous sheath is not released by the further latch fingers 34 until the latching fingers 22 have safely engaged in the windows 46 of the next sheath. As noted, release of the previous sheath provides positive confirmation that the next sheath has been safely clasped. At that stage the previous sheath may be disposed of simply by holding the injection device with the trumpet of the sheath remover facing downwardly.

Thereafter, the next sheath can be removed by pulling the sheath remover away from the injection device as shown in FIG. 7. As shown in FIG. 8, pending loading of a new syringe into the injection device, the sheath remover with clasped sheath can be inserted into the end of the injection device to act as a cover or cap. The shoulder protrusions 28 have latch surfaces 48 for this purposes which latch into the forward end of the penetration depth adjuster 16 (see FIGS. 13a and b).

Referring now to FIGS. 11 and 12a and b, these show the sheath clamping region of the sheath remover 18 clasping a sheath 26. It will be seen that in FIG. 11, two of the latching fingers 22" are in engagement with the window 46 that is visible. The number of latching fingers is selected to ensure there is at least one latch in each window at any time. FIG. 12a shows a condition where two latching fingers 22 are latched in each window 46 and FIG. 12b shows a configuration where just one latch finger 22 is latched in each window 46.

The invention claimed is:

1. A sheath remover for use in removing a sheath from a needle of a syringe prior to an injection, said sheath remover comprising:

an elongate sheath passageway having a sheath capture region at a first end and configured to allow passage of a sheath along the passageway away from the sheath capture region to exit the passageway at a second end to be released from the sheath remover, the second end being opposite to the first end;

a sheath gripping arrangement disposed in said sheath capture region and adapted in use to be engageable with a needle sheath when offered up thereto and to grip the sheath sufficiently to enable to the sheath remover to remove the sheath from the needle as the sheath remover is pulled away from the syringe, wherein said sheath remover is adapted such that, in use, a sheath already disposed in the sheath capture region is pushed along the passage, away from the sheath capture region, when the sheath remover is offered up to, and engages a subsequent sheath.

2. A sheath remover according to claim 1, wherein said elongate sheath passageway comprises a solid-walled tube open at least one end.

3. A sheath remover according to claim 1, wherein said sheath gripping arrangement comprises one or more latching elements designed to latch over a shoulder or recess on the sheath as the sheath remover is offered up to the sheath in use, but allowing movement of a retained sheath away from said sheath capture region further into the passageway.

4. A sheath remover according to claim 3, wherein said one or more latch elements comprise a plurality of latch fingers.

5. A sheath remover according to claim 3, for use with a sheath having diametrically opposed windows in a generally cylindrical portion, wherein each window subtends a given arc, wherein said latch fingers are disposed equi-angularly around the axis of the cylinder and at a pitch to ensure that at least two latch fingers engage into each window.

6. A sheath remover according to claim 1, which includes a further gripping arrangement within said passageway spaced down the passageway from said first mentioned gripping arrangement and designed to slideably engage a sheath that is being moved further into the passageway by introduction of a subsequent sheath into the sheath capture region.

7. A sheath remover according to claim 6, wherein said further gripping arrangement is disposed longitudinally from said first gripping arrangement by a distance, having regard to the length of the sheath, such that a subsequent sheath pushes a previous sheath clear of the second gripping arrangement to release the previous sheath to pass freely along the passageway only when the subsequent sheath has been securely engaged by said first mentioned gripping arrangement.

8. A sheath remover according to claim 1, wherein at least part of the walls making up the passageway are at least one of transparent and apertured, such that a sheath displaced by a subsequent sheath is exteriorly visible.

9. A sheath remover according to claim 1, wherein said sheath remover is removably attachable to said syringe housing in use.

10. A sheath remover according to claim 2, wherein said sheath gripping arrangement comprises one or more latching elements designed to latch over a shoulder or recess on the sheath as the sheath remover is offered up to the sheath in use, but allowing movement of a retained sheath away from said sheath capture region further into the passageway.

11. A sheath remover according to claim 2, which includes a further gripping arrangement within said passageway spaced down the passageway from said first mentioned gripping arrangement and designed to slideably engage a sheath that is being moved further into the passageway by introduction of a subsequent sheath into the sheath capture region.

12. A sheath remover according to claim 3, which includes a further gripping arrangement within said passageway spaced down the passageway from said first mentioned gripping arrangement and designed to slideably engage a sheath that is being moved further into the passageway by introduction of a subsequent sheath into the sheath capture region.

13. A sheath remover according to claim 4, which includes a further gripping arrangement within said passageway spaced down the passageway from said first mentioned gripping arrangement and designed to slideably engage a sheath that is being moved further into the passageway by introduction of a subsequent sheath into the sheath capture region.

14. A sheath remover according to claim 5, which includes a further gripping arrangement within said passageway spaced down the passageway from said first mentioned gripping arrangement and designed to slideably engage a sheath that is being moved further into the passageway by introduction of a subsequent sheath into the sheath capture region.

15. A sheath remover according to claim 2, wherein at least part of the walls making up the passageway are at least one of transparent and apertured, such that a sheath displaced by a subsequent sheath is exteriorly visible.

16. A sheath remover according to claim 3, wherein at least part of the walls making up the passageway are at least one of transparent and apertured, such that a sheath displaced by a subsequent sheath is exteriorly visible.

17. A sheath remover according to claim 4, wherein at least part of the walls making up the passageway are at least one of transparent and apertured, such that a sheath displaced by a subsequent sheath is exteriorly visible.

18. An injection device assembly comprising a housing, a syringe locatable within the housing in use and having a needle covered by a removable sheath, and a sheath remover for removing said sheath, said sheath remover comprising:

an elongate sheath passageway having a sheath capture region at a first end and configured to allow passage of a sheath along the passageway away from the sheath capture region to exit the passageway at a second end to be released from the sheath remover, the second end being opposite to the first end;

a sheath gripping arrangement disposed in said sheath capture region and adapted in use to be engageable with a needle sheath when offered up thereto and to grip the sheath sufficiently to enable to the sheath remover to remove the sheath from the needle as the sheath remover is pulled away from the syringe, wherein said sheath remover is adapted such that, in use, a sheath already disposed in the sheath capture region is pushed along the passage, away from the sheath capture region, when the sheath remover is offered up to, and engages a subsequent sheath.

19. An injection device according to claim 18 wherein said injection device is constructed and arranged to be cocked by inserting a portion of said sheath remover into said injection device and using said sheath remover to energise an internal drive mechanism.

20. An injection device according to claim 18, wherein said injection device comprises a depth adjustment collar movably mounted on a forward portion of said housing to adjust the penetration depth of the needle when the device is actuated, and wherein introduction of said needle sheath remover into said device is prevented unless the depth penetration is set at or beyond a preset level.

21. A sheath remover for use in removing a sheath from the needle of a syringe, prior to an injection, said sheath remover comprising:

an elongate sheath passageway having a sheath capture region at a first end and configured to allow passage of a sheath along the passageway away from the sheath capture region to exit the passageway at a second end to be released from the sheath remover, the second end being opposite to the first end;

a first sheath gripping arrangement disposed in said sheath capture region and adapted in use to be engageable with a needle sheath when offered up thereto and to grip the sheath sufficiently to enable to the sheath remover to remove the sheath from the needle as the sheath remover is pulled away from the syringe and a second sheath gripping arrangement within said passageway spaced from said first mentioned gripping arrangement and designed to slideably engage a sheath that is being moved further into the passageway by introduction of a subsequent sheath into the sheath capture region, wherein in use, a sheath already disposed in the sheath capture region is pushed along the passage, away from the sheath capture region, when the sheath remover is offered up to, and engages a subsequent sheath.

22. A sheath remover according to claim 21, wherein said second sheath gripping arrangement is disposed longitudinally from said first gripping arrangement by a distance, having regard to the length of the sheath, such that a subsequent sheath pushes a previous sheath clear of the second gripping arrangement to release the previous sheath to pass freely along the passageway only when the subsequent sheath has been securely engaged by said first mentioned gripping arrangement.

* * * * *